United States Patent
Parker

(10) Patent No.: US 6,672,305 B2
(45) Date of Patent: Jan. 6, 2004

(54) SHALLOW THROAT OROTRACHEAL INTUBATION GUIDE

(75) Inventor: Jeffrey D. Parker, Cincinnati, OH (US)

(73) Assignee: Parker Medical Limited Partnership, Cincinnati, OH (US)

( * ) Notice: Subject to any disclaimer, the term of this patent is extended or adjusted under 35 U.S.C. 154(b) by 92 days.

(21) Appl. No.: 09/793,162

(22) Filed: Feb. 26, 2001

(65) Prior Publication Data

US 2002/0117171 A1 Aug. 29, 2002

(51) Int. Cl.[7] .............................................. A61M 16/00
(52) U.S. Cl. ............................ 128/200.26; 128/207.14; 128/207.15
(58) Field of Search ....................... 128/200.26, 207.14, 128/207.15; 600/185, 194, 190, 196; 604/108

(56) References Cited

U.S. PATENT DOCUMENTS

| | | | |
|---|---|---|---|
| 2,463,149 A | * 3/1949 | Caine | 128/200.26 |
| 2,541,402 A | * 2/1951 | Caine | 128/200.26 |
| 3,154,069 A | * 10/1964 | Ring | 600/190 |
| 3,314,431 A | * 4/1967 | Smith | 128/200.26 |
| 3,754,554 A | 8/1973 | Felbarg | |
| 3,756,244 A | 9/1973 | Kinnear et al. | |
| 3,802,440 A | 4/1974 | Salem et al. | |
| 3,874,377 A | 4/1975 | Davidson | |
| 3,908,665 A | 9/1975 | Moses | |
| 3,930,507 A | 1/1976 | Berman | |
| 3,943,920 A | 3/1976 | Kandel | |
| 3,948,255 A | 4/1976 | Davidson | |
| 4,068,658 A | 1/1978 | Berman | |
| 4,076,018 A | 2/1978 | Heckele | |
| 4,155,365 A | 5/1979 | Boslau | |
| 4,166,468 A | 9/1979 | Haynie | |
| 4,167,946 A | 9/1979 | Sandstrom | |
| 4,211,234 A | 7/1980 | Fisher | |
| 4,231,365 A | 11/1980 | Scarberry | |
| 4,256,099 A | 3/1981 | Dryden | |

(List continued on next page.)

FOREIGN PATENT DOCUMENTS

| | | |
|---|---|---|
| EP | 0233761 | 8/1987 |
| EP | 0234847 | 9/1987 |
| FR | 2293180 | 7/1976 |
| FR | 2489686 | 9/1981 |
| GB | 1535060 | 12/1978 |
| GB | 2137096 | 10/1984 |
| GB | 2205499 | 12/1988 |
| GB | 2229367 | 9/1990 |
| WO | WO 89/02719 | 4/1989 |
| WO | WO 99/39762 | 8/1999 |

OTHER PUBLICATIONS

*Anasthesiology Review*, p. 24, vol. III, No. 1.
Bleyer, J. Mount, *Some Practical Hints in Connection with Intubation of the Larynx, and a Resume of 206 Cases Operated on From 1886 to 1888*, N.Y. Med. Jour., Feb. 2, 1889, pp. 122–125.
Bleyer, J. Mount, *Tongue and Larynx Tractor for the Performance of Forced Laryngoscopy in Children. Mouth–gag and Cupped–out Intubation Tube with False Metal Epiglottis Attachment*, Archives of Pediatrics, pp. 597–599 (Oct. 1888).

(List continued on next page.)

*Primary Examiner*—Weilun Lo
*Assistant Examiner*—Joseph F. Weiss, Jr.
(74) *Attorney, Agent, or Firm*—Wood, Herron & Evans, LLP

(57) ABSTRACT

A blind intubation guide (10) includes a guide wall (42), which aims an orotracheal tube (120) into the laryngeal opening (230), the guide wall (42) being pivotally mounted to an aft member (16) of the guide (10) to accommodate throats (202) of variable shallowness. The guide (10) may also include a flexible spout (100).

32 Claims, 7 Drawing Sheets

U.S. PATENT DOCUMENTS

| | | | |
|---|---|---|---|
| 4,279,246 A | | 7/1981 | Chikama |
| 4,306,547 A | | 12/1981 | Lowell |
| 4,338,930 A | | 7/1982 | Williams |
| 4,360,008 A | * | 11/1982 | Corazzelli, Jr. ............. 600/190 |
| 4,365,625 A | | 12/1982 | Rind |
| 4,384,570 A | | 5/1983 | Roberts |
| 4,497,318 A | | 2/1985 | Donmichael |
| 4,509,514 A | | 4/1985 | Brain |
| 4,553,540 A | | 11/1985 | Straith |
| 4,573,451 A | * | 3/1986 | Bauman ..................... 600/190 |
| 4,612,927 A | * | 9/1986 | Kruger ................. 128/200.26 |
| 4,655,214 A | | 4/1987 | Linder |
| 4,672,960 A | | 6/1987 | Frankel |
| 4,683,879 A | | 8/1987 | Williams |
| 4,685,457 A | | 8/1987 | Donenfeld |
| 4,773,394 A | | 9/1988 | Reichstein et al. |
| 4,793,327 A | | 12/1988 | Frankel |
| 4,809,680 A | | 3/1989 | Yabe |
| 4,825,858 A | | 5/1989 | Frankel |
| 4,832,020 A | | 5/1989 | Augustine |
| 4,840,172 A | | 6/1989 | Augustine et al. |
| 4,919,126 A | | 4/1990 | Baildon |
| 5,024,218 A | | 6/1991 | Ovassapian et al. |
| 5,035,231 A | | 7/1991 | Kubokawa et al. |
| 5,038,766 A | | 8/1991 | Parker |
| 5,042,469 A | | 8/1991 | Augustine |
| 5,174,283 A | | 12/1992 | Parker |
| 5,193,544 A | | 3/1993 | Jaffe |
| 5,203,320 A | | 4/1993 | Augustine |
| 5,339,805 A | | 8/1994 | Parker |
| 5,400,771 A | | 3/1995 | Pirak et al. |
| 5,448,990 A | | 9/1995 | De Faria-Correa |
| 5,498,231 A | * | 3/1996 | Franicevic ................. 600/190 |
| 5,533,496 A | | 7/1996 | De Faria-Correa et al. |
| 5,605,532 A | | 2/1997 | Schermerhorn |
| 5,720,275 A | * | 2/1998 | Patil et al. ............. 128/200.26 |
| 5,743,254 A | | 4/1998 | Parker |
| 5,845,634 A | | 12/1998 | Parker |
| 6,053,166 A | * | 4/2000 | Gomez .................. 128/200.26 |
| 6,079,409 A | * | 6/2000 | Brain ..................... 128/200.26 |
| 6,311,688 B1 | * | 11/2001 | Augustine et al. ...... 128/200.26 |
| 6,386,199 B1 | * | 5/2002 | Alfery .................... 128/207.15 |
| 6,427,686 B2 | * | 8/2002 | Augustine et al. ...... 128/200.26 |

OTHER PUBLICATIONS

Brain, A.I.J., *Three Cases of Difficult Intubation Overcome by the Laryngeal Mask Airway*, Anaesthesia, 1985, vol. 40, pp. 353–355.

Brain, A.I.J., *The Laryngeal Mask– A New Concept in Airway Management*, Br. J. Anaesth. (1983), vol. 55, pp. 801–805.

*Fundamentals of Tracheal Intubation*, pp. 74–76 and FIGS. 4–9 at p. 56.

Knapp, *A Director for the Stomach Tube*, Med. Record N.Y., 322, Aug. 29, 1986.

Liban, J.B. et al., *A New Blade for Endotracheal Intubation*, British Journal of Anaesthesia, vol. 49, pp. 1279–1280 (1977).

Leroy, *Recherches Sur L'Asphyxie*, 7 J. de Physiologique, 45, 65, 1827.

Machida, *The Next Generation Nasopharyngo–Laryngoscopes*.

*Rusche Super Safety Clear Endotracheal Tubes*.

*Understanding Anesthesia Equipment*, pp. 342–343 and 346–349.

International Search Report, (PCT/US01/12056), (four pages).

\* cited by examiner

SHALLOW THROAT OROTRACHEAL INTUBATION GUIDE

BACKGROUND OF THE INVENTION

I. Field of the Invention

The present invention relates to orotracheal intubation guides and more particularly to blind intubation guides for insertion of an orotracheal tube into a patient's trachea, especially in the case of patients having a shallow throat.

II. Description of Prior Art

When a patient stops breathing, it is imperative that effective ventilation be instituted as soon as possible. Ventilation is best accomplished by forcing air through an orotracheal tube inserted through the mouth and laryngeal opening and into the trachea. A blade laryngoscope is commonly employed to provide such insertion. But the blade laryngoscope can be slow and difficult to use. The blade laryngoscope further requires manual visualization of the vocal cords so as to facilitate insertion of the tube. Use of blade laryngoscopes often results in dental and airway trauma and accidental insertion of the tube into the esophagus instead of the trachea. Such misintubation, if not quickly recognized and corrected, may have fatal consequences.

Blind intubation guides have been developed as an alternative to blade laryngoscopes. The goal of blind intubation guides is to eliminate the need for visualization of the vocal cords, and to reduce the risk of trauma and injury to patients which occurs with the use of blade laryngoscopes. I have developed several blind intubation guides which not only minimize such injury and trauma, but also substantially reduce the risk of misintubation. Such advantageous blind intubation guides are described in my U.S. Pat. Nos. 5,339,805 and 5,743,254, the disclosures of which are incorporated herein in their entirety.

The guides of my '805 and '254 patents have an elongated aft portion or member in which the orotracheal tube is mounted. The distal end of the aft member includes a support portion depending therefrom and designed to fit against the back of the patient's tongue in or above the valleculae and in front of the epiglottis. The underside of the aft member may function as a tongue-depressor to hold the tongue down against the floor of the mouth. The guides further include a guide wall connected to the aft member and spaced forwardly of the support portion. The guide wall is designed to be positioned at the back of the throat to provide a bearing surface which directs the orotracheal tube downward into the laryngeal opening and trachea when the support portion is properly seated behind the tongue. To avoid snagging of the epiglottis by the tube and/or the tendency of the epiglottis to block the glottic opening, the guide may be provided with a spout extending from the aft member and towards the guide wall as described in my '254 patent.

With the guides of my prior patents, intubation may thus be accomplished more reliably, and without substantial risk of trauma or misintubation as often occurred with blade laryngoscopes and other blind intubation guides. The guides of my prior patents are believed to accommodate most throat depths. In some instances, however, the throat may be very shallow such that the space between the back of the patient's tongue and the rear wall of the throat is limited. In these cases, the guide wall can impact the rear wall of the throat preventing the support member from being advanced into the retroglossal space, i.e., the space behind the tongue. As a result, the guide cannot be properly seated therein, and the guide wall may not be properly aligned to direct the tube into the larynx. If the guide is simply made smaller to accommodate the shallow throat, then there may not be sufficient space between the guide wall and support member to pass the tube therethrough and into the larynx.

SUMMARY OF THE INVENTION

The present invention provides an improved blind intubation guide which overcomes the problems encountered in shallow throat situations. To this end, and in accordance with the principles of the present invention, the guide wall of the intubation guide is pivotally mounted to the aft member so that as the guide wall impacts against the rear wall of the throat, it can pivot so as to thereby decrease the spacing between the guide wall and the support member, from the normally desired spacing for a tube to fit through, to a lesser spacing as necessary to allow both the guide wall and the support member to fit simultaneously in the back of the throat and into the retroglossal space. With the guide wall thus pivoted, the support member can be advanced further into the throat so as to be placed behind the back of the tongue. Subsequent forward traction against the back of the tongue by the support member displaces the tongue forwardly thereby enlarging the space behind the tongue so that it is sufficient for normal placement of the guide wall and support member. With forward traction of the tongue by the support member, the guide wall is released from against the rear wall of the throat. The guide wall is thus enabled to pivot or be pivoted back toward its original position. The original space between the guide wall and the support member is thus reopened to allow the tube to pass therethrough and to allow the guide wall to achieve the desired alignment with the larynx. The tube, normally mounted to the aft member and the guide wall, is resilient and may be utilized to cause the guide wall to pivot back toward its original position as traction is applied to the back of the tongue.

The guide wall may be rigidly affixed to a side arm that is pivotally mounted to the aft member. The arm may include a mounting post member that is rotatably received in a post receiving channel formed in the aft member, such as in the support member near the upper end thereof. Stop structure may also be provided in the aft member and the side arm to limit the range of pivoting of the guide wall relative to the aft member.

The guide may also advantageously include a spout as taught in my '254 patent. In accordance with a further aspect of the present invention, the spout is adapted to yield by flexing or deforming in response to pressure exerted by or through the tube. To that end, as the guide wall pivots towards the support member, the orotracheal tube mounted in the guide will be pushed against the spout by the guide wall and will cause the spout to yield by flexing or deforming. Yielding of the spout to pressure from the tube will prevent the tube from becoming unduly bent by or around the spout in a manner that could damage the tube or an instrument such as a fiberoptic bundle contained therein. As forward traction is applied by the support member to the back of the tongue, the pressure of the guide wall against the tube and the resulting pressure of the tube against the spout are simultaneously released. The spout is advantageously resilient such that the spout will flex back toward its original form and position. As the spout returns to its original pre-flexed form and position, it pushes the tube against the guide wall, causing the guide wall to pivot back toward its original pre-pivoted position.

By virtue of the foregoing, there are thus provided improvements to blind intubation guides that have the advantages of my prior patented blind intubation guides but which can readily accomodate shallow throats. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTIONS OF THE DRAWINGS

Figure 1:
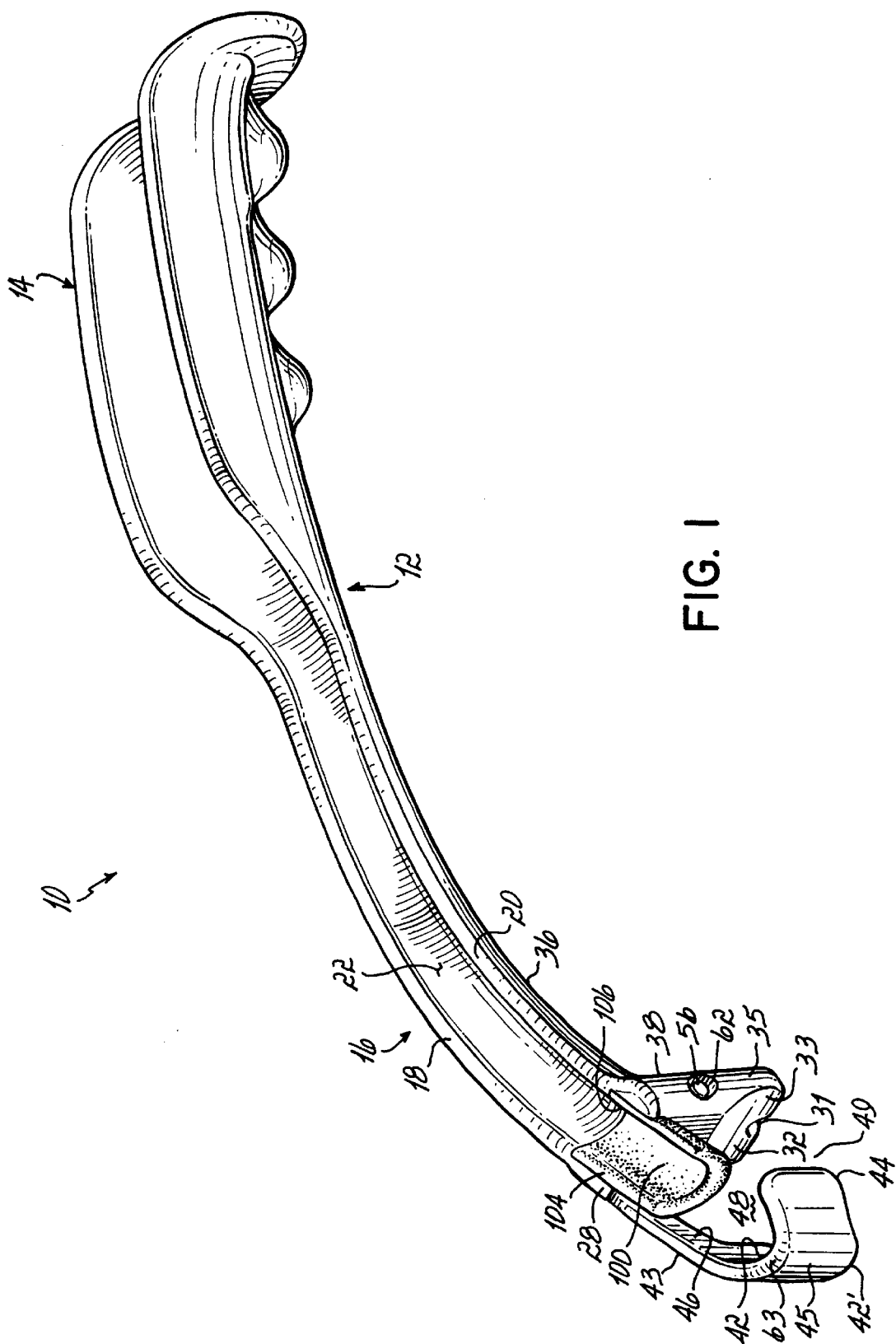
FIG. 1 is a perspective view from the left of a blind intubation guide in accordance with the principles of the present invention.
Figure 2:
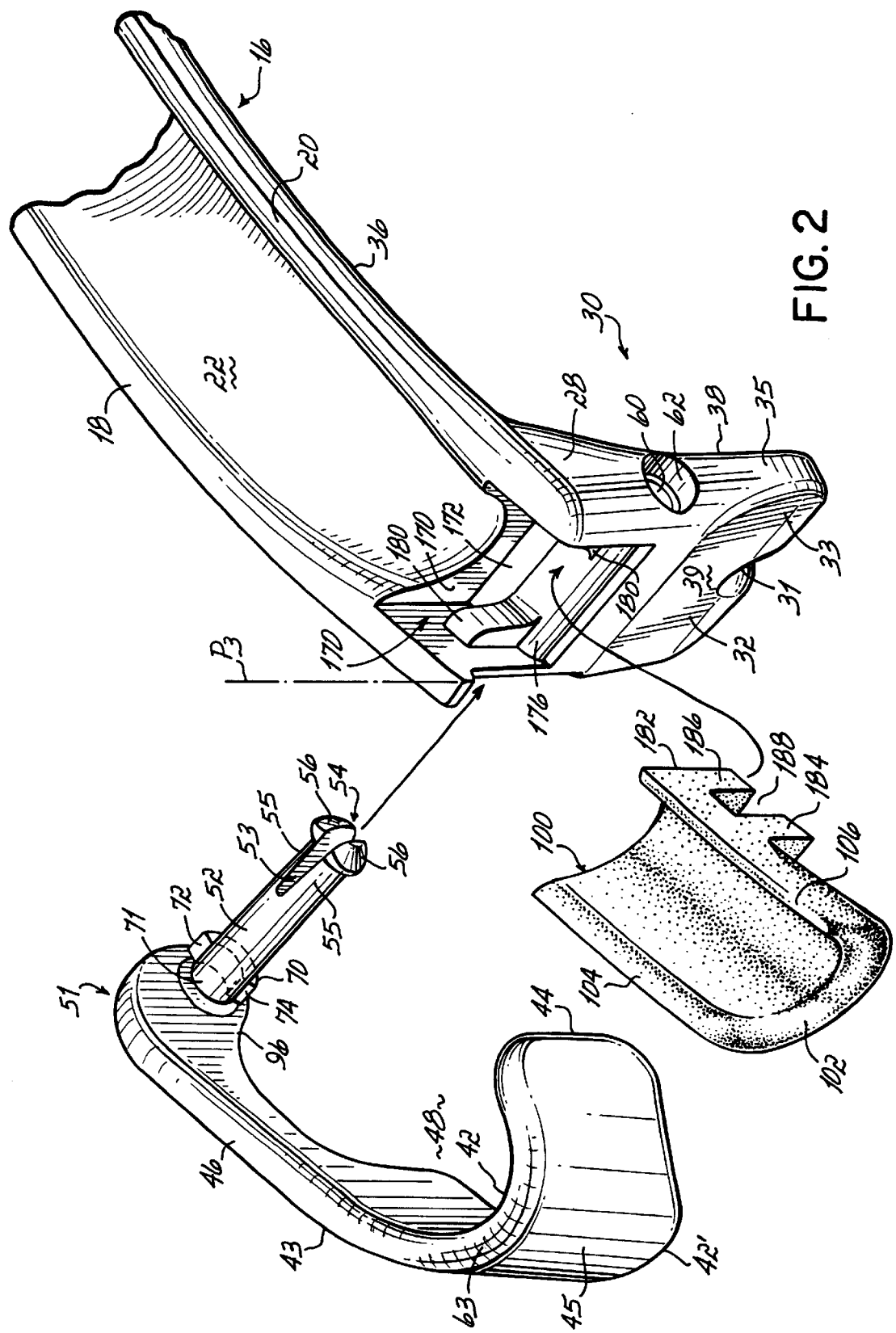
FIG. 2 is an exploded, partial view of the guide of FIG. 1.
Figure 3:
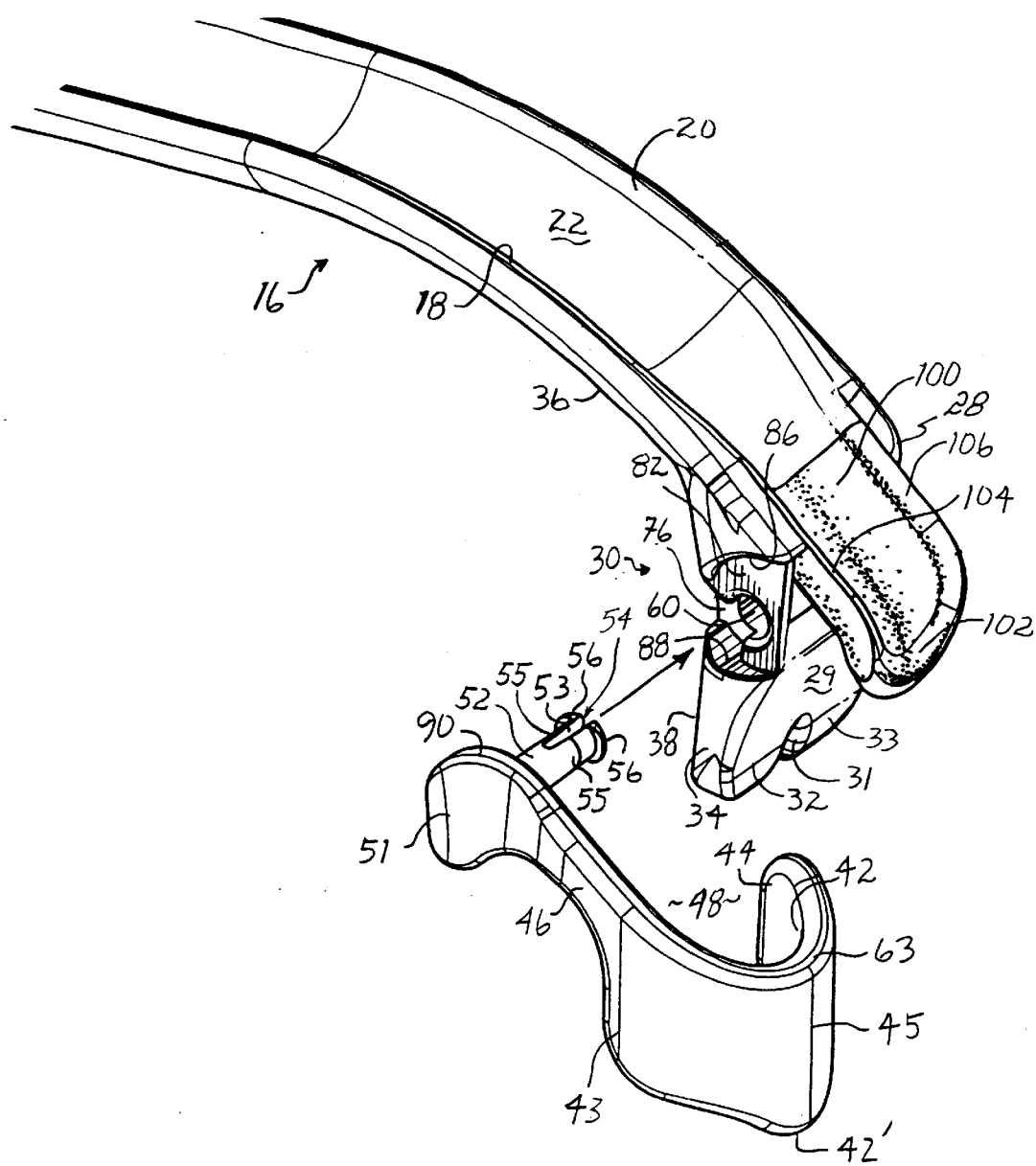
FIG. 3 is a partial, exploded view of the guide of FIG. 1 from the right.

With reference to FIGS. 1 to 3, there is shown a blind intubation guide 10 according to the principles of the present invention. Guide 10 includes a main member 12 having a proximal handle portion 14 and an elongated aft portion or member 16. Aft portion 16 has a generally U-shaped cross-section or groove having right and left side walls 18 and 20 and floor 22, the latter of which extends in a generally horizontal, albeit somewhat arcuate, orientation as depicted in FIG. 1. Side walls 18, 20 and floor 22 may extend or merge with handle portion 14 as desired. Aft member 16 includes, depending in a generally vertical orientation from the distal end 28 thereof, a support portion or member 30. Support portion 30 may be a solid wall with a medial notch 31 therein to define a pair of spaced-apart legs 32, 33. Support portion 30 may have a width of 3 to 5 mm (tapering down to legs 32, 33) to define right and left side surfaces 34, 35. Legs 32, 33 may be approximately 25 mm long, although longer legs, as shown in my '805 and '254 patents, or shorter legs depending on whether the guide is sized for use in adults, children or infants, may be used. The underside surface 36 of aft member 16 merges continuously into backside 38 of support portion 30 and defines a tongue-depressing surface of guide 10. The front side 39 of support portion 30 may be flat with a taper at legs 32, 33.

Spaced forwardly of support portion 30 is a generally vertically disposed guide wall 42 which has a generally concave cross-section between right and left extents or edges 43, 44 of guide wall 42. Guide wall 42 is mounted to aft member 16 so as to pivot relative to support member 30 to thereby vary the distance D therebetween as will be explained below with reference to FIGS. 4A and 4B. Guide wall 42 may also include a depending cusp 42' at its outermost extent 45 from support 30. Integrated with and extending from extent 43 of guide wall 42 is a rigid side arm 46. Side arm 46 is also pivotably or rotatably mounted to aft member 16 such as at distal end 28 thereof to thereby provide for pivot action of guide wall 42. Arm 46 spaces support portion 30 and guide wall 42 apart to define a tube-receiving space 48 therebetween having a variable distance D depending upon the pivot position of wall 42. The free vertical edge 44 of wall 42 is spaced opposite left side 35 of support portion 30 to define a tube-removal gap 49 (FIG. 1) therebetween. The width of gap 49 should be no more than 2-3 mm less than the outer diameter of the largest orotracheal tubes 120 (see FIG. 5) intended to be passed through that gap, in order for such tube to be laterally removable from space 48 through gap 49.

Arm 46 may include at its proximal end 51 a transverse axle or rotation post 52. As best seen in FIG. 2, rotation post 52 advantageously includes a slot 53 extending from its distal end 54 to define spring action parallel branches 55, each with a projecting retention barb 56 at distal end 54. Post 52 may be inserted through rotation post hole 60 formed through the upper extent of support member 30 at distal end 28 of aft member 16, such as through right side 34 above legs 32, 33. Post hole 60 is advantageously sized to be have a diameter slightly larger than axle 52, but less than the outermost diameter of barbs 56 when they are biased outwardly as is normal. With post 52 inserted through post hole 60, guide wall 42 is thus pivotally mounted to distal end 28 of aft member 16. Post hole 60 may terminate on the left side 35 of support member 30 above leg 33 in an enlarged opening or counterbore 62 sized to receive barbs 56 as expanded to thereby lock post 52 to aft member 16. Axle 52 is advantageously of a length such that barbs 56 fit in counterbore 62 and are recessed from the left side surface 35 of support member 30.

Figure 4A:
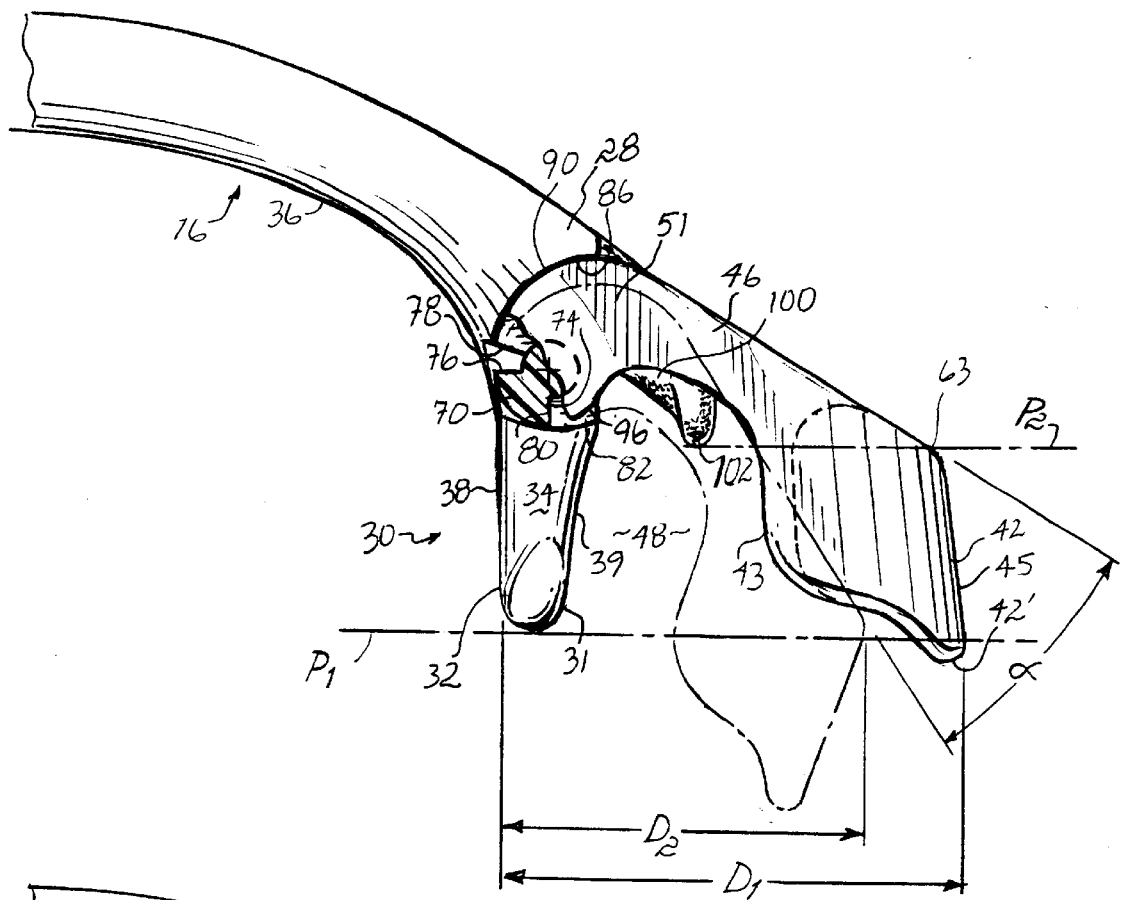
FIGS. 4A and 4B are partial, right side elevation views of the guide of FIG. 1 showing a pivot action of the guide wall.
Figure 4B:
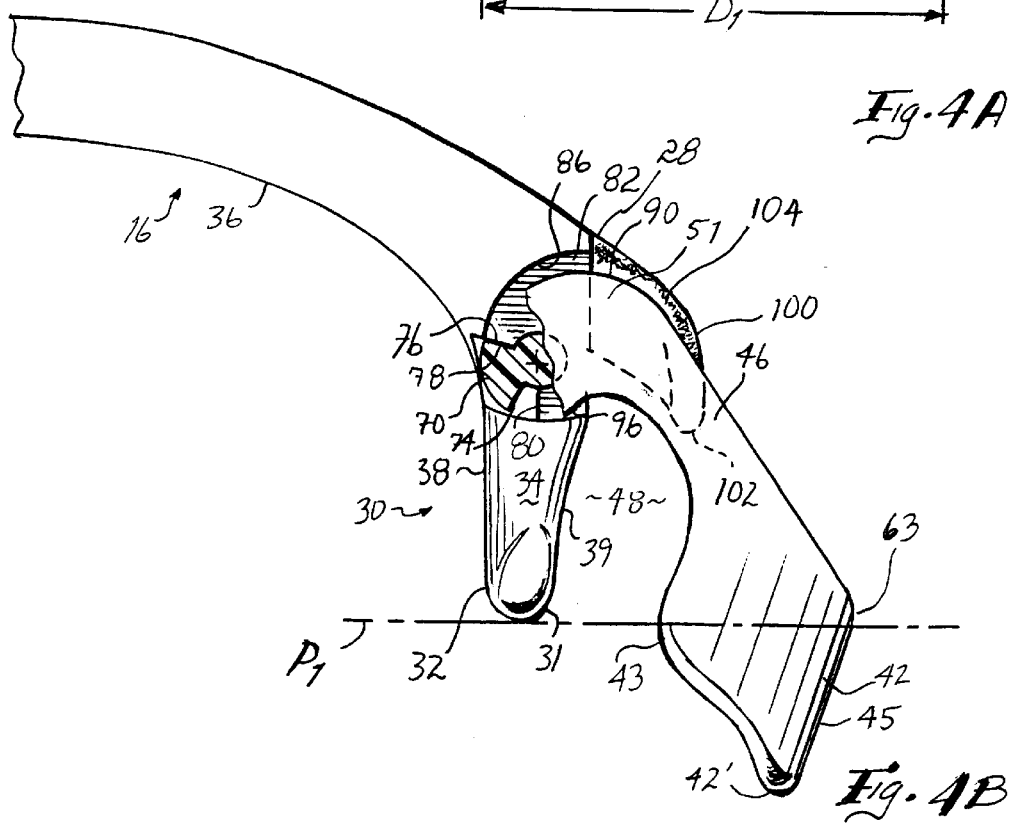

With guide wall 42 pivotally mounted to aft member 16, as side arm 46 rotates on axle 52, guide wall 42 will pivot from a normal or first position as shown in solid line in FIG. 4A towards a second or shallow throat position shown in solid line in FIG. 4A and dotted line in FIG. 4B. As can be seen, in the first position of guide wall 42 relative to support member 30, the lateral distance of tube guiding space 48 is of a length $D_1$ whereas in the pivoted or second position, the distance is decreased to distance $D_2$. Advantageously, guide wall 42 can pivot through an angle $\propto$ of about 27°. In the first, or normal, position of guide wall 42, cusp 42' is confronting medial notch 31 with cusp 42' in or adjacent to a horizontal plane $P_1$ transverse to the ends of legs 32, 33 (FIG. 4A), whereas cusp 42' is spaced well below the horizontal plane $P_1$ in the second, or shallow throat, position (FIG. 4B) such that the upper edge 63 of guide wall 42 at outermost extent 45 is near plane $P_1$. To limit pivot action to the desired range between the first and second positions, cooperating stop structure is provided for arm 46 and aft member 16, two embodiments of which will be described herein.

One stop structure is provided by a rotation stop block 70 formed on the interior of distal end 51 of arm 46 and partially surrounding a proximal end 71 of post 52 (FIG. 2), and a stop block socket 76 on the right side 34 at the distal end 28 of right wall 18 and support member 30 (FIG. 3). Rotation stop block 70 has an anterior shoulder 72 and a posterior shoulder 74, with an angle of the planes therebetween defined to approximate angle α. Stop block socket 76 has an upper border 78 and a lower border 80 which are designed to confront shoulder 72 and 74 of stop block 70 depending upon the position of guide wall 42. To this end, as seen in FIG. 4A, in the first position of guide wall 42, shoulder 74 abuts lower edge 80 of socket 76 so that guide wall 42 cannot be pivoted upwardly out of the first position. As guide 42 is pivoted from the first position shown as solid line in FIG. 4A to the second position (shown as dashed line in FIG. 4A and solid line in FIG. 4B), shoulder 74 and edge 80 are moved apart and shoulder 72 is brought towards, and may ultimately be brought into, abutting relationship with edge 78 to thereby limit pivoting of guide wall 42 so that it will not go beyond the second position.

Another stop structure is provided by the interaction of side arm 46 with aft member 16. To this end, a recess or shoulder socket 82 is formed in support member 30 at distal end 28 and is recessed from the right surface 34 of support member 30 by a distance equal to about the thickness of distal end 51 of arm 46, with recess 76 being further therein to receive stop block 70 as above described. Recess 82 has an upper border 86 and a lower border 88. Upper border 86 cooperates to impact against the upper surface or shoulder 90 of distal end 51 of side arm 46 so as to further limit over-rotation or over-pivoting of guide wall 42 upwardly out of the first position. Additionally, the underside 96 of the distal end 51 defines a second shoulder which in the first position of guide wall 42 is spaced slightly above the lower border 88 of socket 82. Lower border 88 provides a bearing surface for shoulder underside 96 as guide wall 42 pivots into the second position to also facilitate limitation of the downward pivot range of guide wall 42.

In one embodiment of guide 10, for an adult throat, distance $D_1$ is advantageously 32.7 mm and distance $D_2$ is advantageously 25.6 mm. Comparable distance relationships may be designed into a guide 10 designed for smaller throats such as for children or infants, for example.

Main member 12 may be a single piece of plastic, and guide wall 42 and side arm 46 and related post 52 may also be a single piece of plastic. These components may be advantageously formed of relatively rigid, medical grade plastic such as by injection molding of polyethylene, polypropylene or ABS. Alternatively, aft member 16 and guide wall 42 may be found as a single device with arm 46 shaped to provide flexure so as to afford guide wall 42 a pivoting action for the purposes described herein.

To facilitate use of guide 10 as described in my aforesaid '254 patent, guide 10 may further include an extended tube-support or spout 100 terminating in a free distal edge 102, which extends into space 48 between support portion 30 and guide wall 42 so as to effectively define a generally horizontal, but somewhat downwardly sloping, continuation of floor 22 of aft member 16. In the first position of guide wall 42, the upper edge 63 of wall 42 at outermost extent 45 is generally in or adjacent to the horizontal plane $P_2$ that extends through free edge 102 (FIG. 4A). Spout 100 thus creates an overhanging eave in space 48. Spout 100 has a generally concave cross-section, the lateral, right side edge 104 of which is adjacent to, but not interconnected with, side arm 46 so that guide wall 42 may pivot without interaction with spout 100. The left side edge 106 of spout 100 may be exposed through gap 49.

Spout 100 may be integrally formed with aft member 16 such as during the injection molding process of forming main member 12. Advantageously, spout 100 is made of a more flexible material than aft member 16 for purposes to be described. Spout 100 may, for example, be of material having a 70 shore A durometer. In that event, spout 100 may be integrally formed with aft member 16, such as by overmolding, or may be separately formed and subsequently attached to aft member 16, such as by glueing or ultrasonic welding.

To secure spout 100 to aft member 16, the junction 170 of support member 30 and aft member 16 may be provided with a spout receiver 172 (FIG. 2) defined as a cavity between walls 18 and 20 at distal end 28, terminal wall 174 of floor 22, and top ledge 176 of support 30. Formed adjacent to walls 18 and 20 in cavity 172, and spaced from wall 174 and a generally vertical plane $P_3$ defined by wall 39 of support 30, are a pair of plastic wedges 180 extending into cavity 172, but below the upper extent of walls 18 and 20. Spout 100 includes at its proximal end 182 a pair of generally vertical depending supports 184, 186 sized to fit around wedges 180 with support 184 aligned with wall 39 of support member 30, and support 186 being against wall 174. The gap 188 between supports 184, 186 is about equal to the thickness of wedges 180 and may be continuous, or discontinuous so as to merge with supports 184, 186, in the space between wedges 180.

Figure 5:
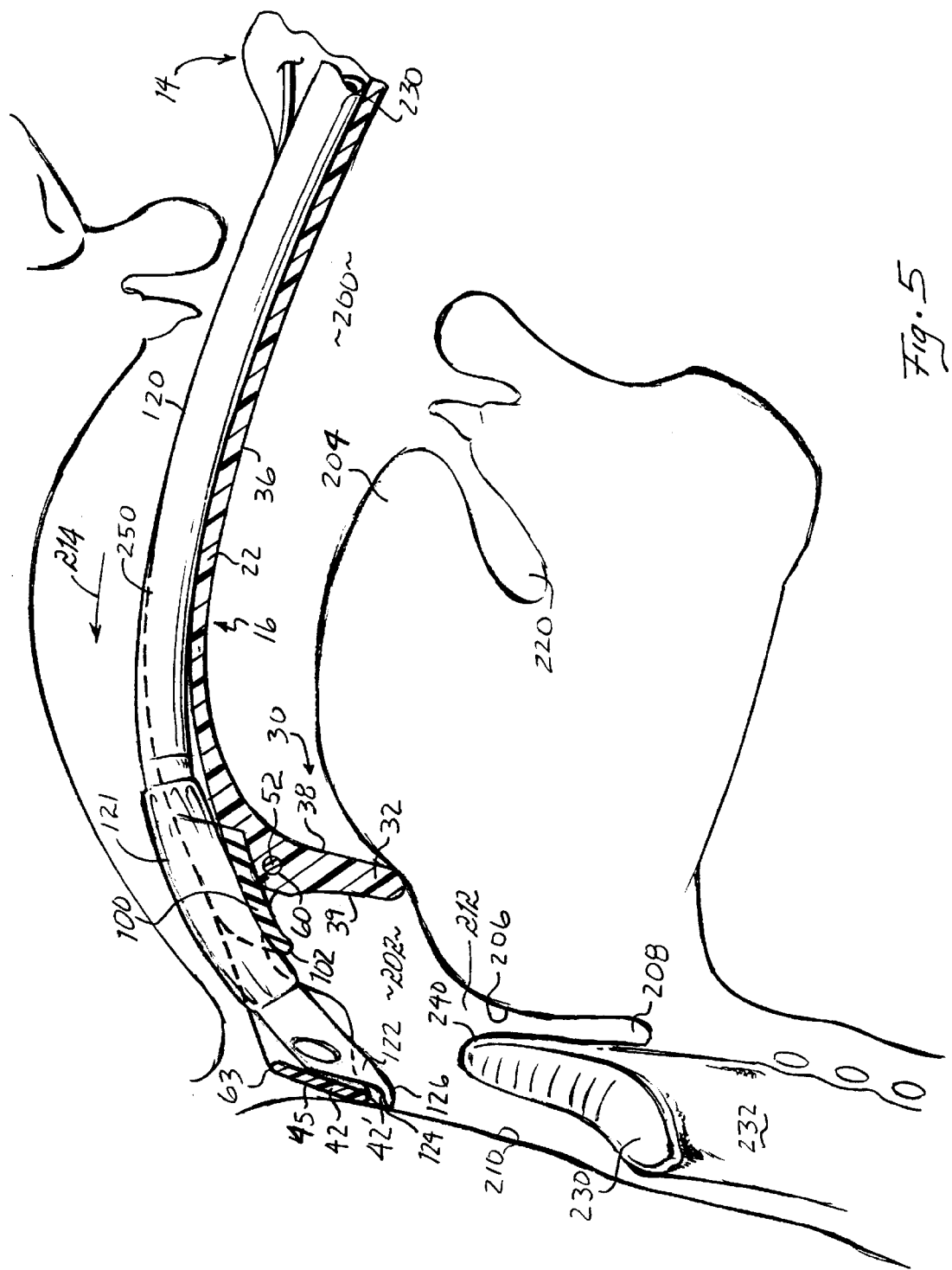
FIG. 5 is a schematic illustration, partially cut-away, showing the guide of FIG. 1 with the guide wall impacting the back of a shallow throat and with an orotracheal tube mounted thereto for purposes of explaining the principles of the present invention.

The upper aspect of member 12 is adapted to receive and support an endotracheal tube 120 (referred to as an orotracheal tube when it is inserted through the mouth as intended here) therein as seen, for example, in FIG. 5. To this end, tube 120 is mounted to aft member 16 and may fit within the U-shaped cross-section of member 12 such that distal tip 122 of tube 120 can be advanced beyond spout 100 and beyond free edge 102 toward guide wall 42 to impact and bear thereagainst. The tube of my U.S. Pat. No. 5,873,362, the disclosure of which is hereby incorporated by reference in its entirety, may be advantageously employed with guide 10. When the tube of my '362 patent is employed, cusp 42' may fit into the opening 124 at distal tip 122 so as to overlie curved lip 126, with lip 126 about 5 mm below cusp 42'. With tube 120 pre-loaded into member 12, guide 10 may be inserted through a patient's mouth 200 and into the throat 202. To this end, and with reference to FIG. 5, while depressing tongue 204 and/or pulling it out of mouth 200, guide 10 is inserted such that legs 32 and 33 of support portion 30 ride over tongue 204 in an effort to place support portion 30 at the back 206 of tongue 204 with legs 32, 33 resting above (or into, if legs 32, 33 are longer) valleculae 208 (only one shown) behind tongue 204. However, in a shallow throat, as seen in FIG. 5, guide wall 42 and outermost extent 45 thereof will impact rear wall 210 of throat 202 before support portion 30 can reach the back 206 of tongue 204.

Figure 6:
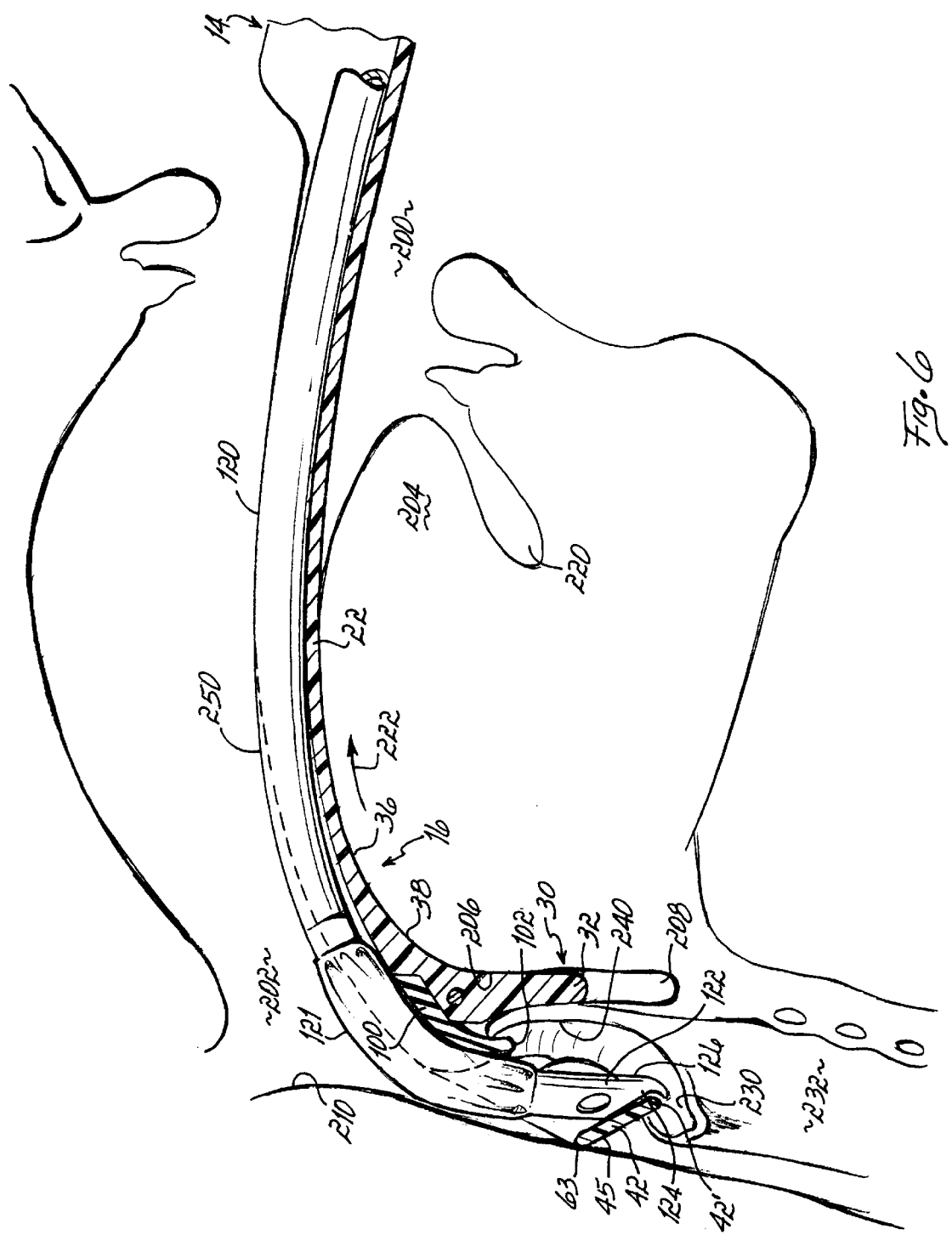
FIG. 6 is a view similar to FIG. 5 showing the guide wall pivoting and the spout flexing to accommodate the shallow throat as the guide is inserted deeper into the throat.

To accommodate the shallow throat, the pivoting nature of guide wall 42 may be advantageously utilized to push guide 10 further into throat 202 to bring support member 30 over the back 206 of tongue 204 into the retroglossal space 212. To this end, further pressure on guide wall 42 by pushing guide 10 further into throat 202 in the direction of arrow 214 against throat rear wall 210 will cause guide wall 42 to pivot from the first position shown in FIG. 5 towards, or all the way into, the second position such as shown in FIG. 6 as support member 30 slides over tongue 204 and into the back 206 thereof. Also, spout 100, if flexible, will yield as seen in FIG. 6, rather than overbend or overstress tube 120 and any components (not shown) therein. With support member 30 now over the back 206 of tongue 204, aft member 16 is supported over tongue 204 by support member 30 while also serving to keep tongue 204 down against the floor 220 of mouth 200. Thereafter, guide 10 may be pulled in a direction away from mouth 200 as indicated by arrow 222 in FIG. 6, to apply forwardly traction at the back 206 of tongue 204 thereby generally aligning space 48 over laryngeal opening 230 in preparation for intubation. Guide wall 42 will be pulled away from throat rear wall 210 thereby relieving the pressure of wall 210 on guide wall 42. Similarly, pressure exerted by guide wall 42 against tube 120, and by tube 120 against spout 100, will be released. The resiliency of spout 100 and tube 120 will urge those structures toward their original positions, and will urge guide wall 42 back towards its original first position. The result is to provide the desired orientation and spacing, as shown in FIG. 7, to guide tube tip 122 relative to laryngeal opening 230 and trachea 232.

Figure 7:
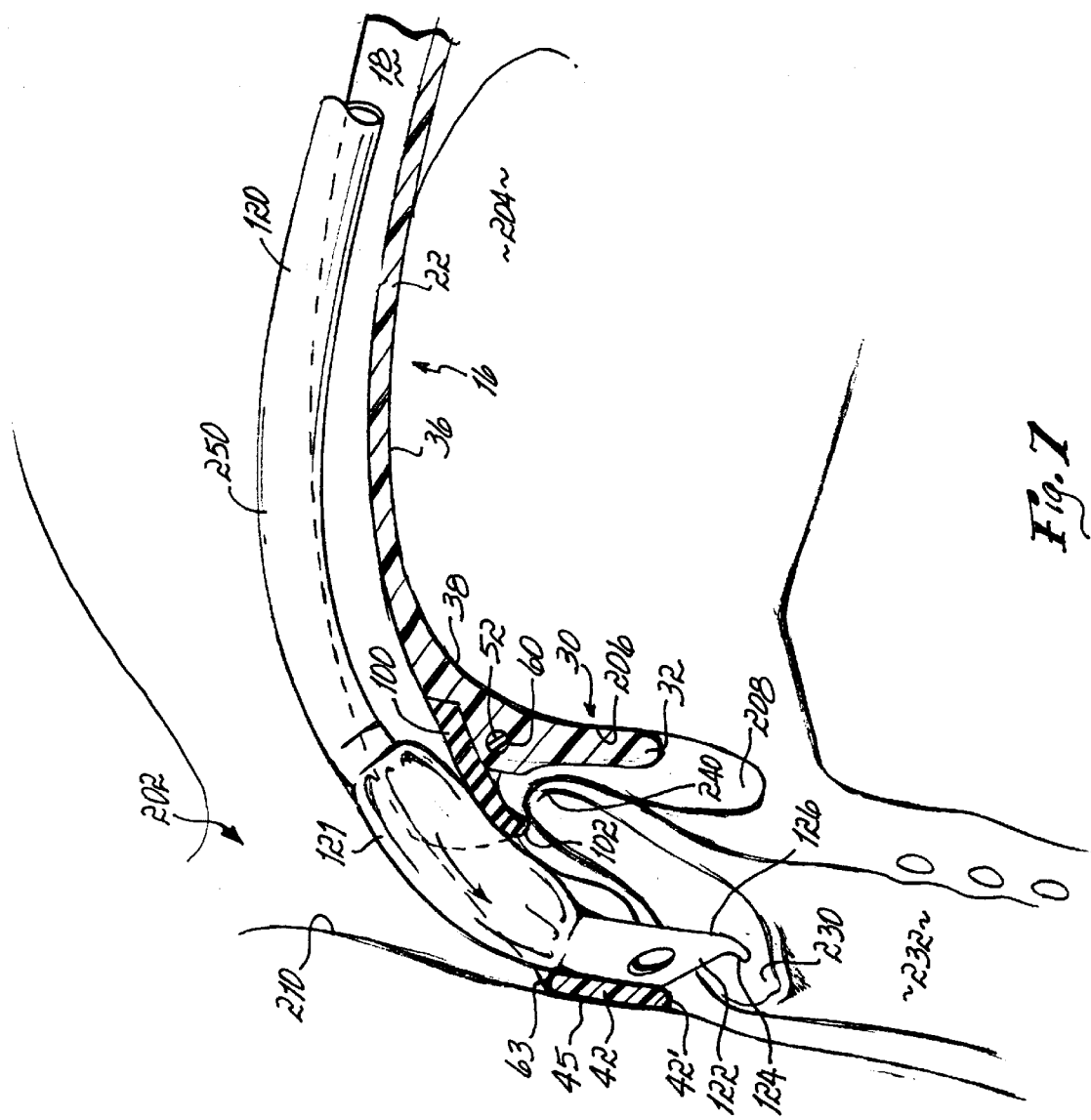
FIG. 7 is a view similar to FIGS. 5 and 6 showing the guide in position after applying traction to the back of the tongue and with the orotracheal tube being advanced along the guide wall into the laryngeal opening.

As guide 10 is being seated in the throat 202 as shown in FIG. 7, the patient's epiglottis 240 is confined to a space below the level of the overhanging eave defined by spout 100. Because orotracheal tube 120 is supported on top of spout 100 and extends beyond the free end 102 thereof, tube 120 is above and beyond the top of epiglottis 240 and so will not collide therewith. Tube tip 122 is against guide wall 42 to cause tube 120 to assume a downward curvature in space 48, thereby positioning tube tip 122 in a generally vertical orientation behind and parallel to epiglottis 240, and in close proximity to rear wall 210 of throat 202. As forward traction is applied to tongue 204 by guide 10, tube tip 122 is pulled closer to the rear surface of epiglottis 240, but does not catch on or collide therewith due to the vertical and parallel relationship above-described. Instead, tube tip 122 may be advanced downward and into and through laryngeal opening 230 behind epiglottis 240 without interference or obstruction from epiglottis 240. Flexibility of spout 100, if a flexible material is used, can also facilitate passage of tubes by yielding to accommodate larger tube diameters through space 48 and easy passage of bulkier cuffs 121 with less risk of cuff tearing.

In use, the forward end of an orotracheal tube 120 may be manually lubricated with a film of sterile, water-soluble, biocompatible lubricant. The lubricated tube 120 is placed in member 12, with tip 122 extending beyond free edge 102 of spout 100 such that the bevel at opening 124 is against guide wall 42. Guide 10 is inserted into the throat 202 and legs 32, 33 are advanced over tongue 204 until aft member 16 rests flush against the upper surface of tongue 204 and support member 30 seats behind tongue 204 such as with legs 32, 33 positioned in or above valleculae 208, or until guide wall 42 impacts throat wall 210, such as in the case of a shallow throat. In the latter event, guide 10 is further slid over tongue 204 until support 30 is over the back 206 thereof. As that movement occurs, guide wall 42 will pivot, and spout 100 may flex. Once support 30 passes over the back 206 of tongue 204, it is pushed downward to seat first against the back 206 of tongue 204, and traction is then applied to guide 10 in order to pull guide wall 42 away from rear wall 210 and cock the epiglottis 240 into a more upright position near paired legs 32, 33 and front side 39, and to allow guide wall 42 to return toward its normal position whereat tube 120 may then be readily guided into the laryngeal opening 230 by pushing on the proximal end 230 of tube 120. Tube 120 will slide off of spout 100 and over the top of epiglottis 240 and downward along guide wall 42. Continued pushing on tube 120 causes the medial portion 250 of tube 120 to rotate over free edge 102 of spout 100 into a more vertical orientation, and then to enter the laryngeal opening 230 and trachea 232, as discussed above. Once the distal end 122 of tube 120 has been advanced to the desired depth in trachea 232, guide 10 may be pulled back over tube 120, and then laterally disengaged from tube 120 through gap 49. Tube 120 is then secured to the patient in the conventional manner.

By virtue of the foregoing, there is thus provided a blind intubation guide that advantageously employs the features of my prior guides whereby to safely and easily intubate a patient while overcoming the problem presented by a shallow throat.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, medial notch 31 may be eliminated. Further, guide 10 may be provided with an endoscope (i.e., a laryngoscope) viewing system by placement of one or more channels (not shown) through guide 10 and terminating in one or more openings (also not shown) in guide wall 42 as described in my '805 patent, or with an endoscope viewing system as described in my U.S. Pat. No. 5,845,634, the disclosure of which in its entirety is incorporated herein by reference. Moreover, while the tube guiding space 48 is shown as collapsing in spacing D as guide wall 42 pivots by articulation, other pivoting actions are possible such as by deformation of guide wall towards support 30. Thus, the term "pivot" as used herein is broadly utilized to encompass transiently varying the distance relationship between the guide wall 42 and support 30 whereby to accommodate a shallow throat by narrowing that distance on insertion of the guide into the back of the throat 204 in order to place support member 30 at the back 206 of the tongue 204, and then re-expanding the distance by placing traction on the tongue 204 with support member 30. The invention in its broader aspects is, therefore, not limited to the specific details, representative apparatus and method, and illustrative example shown and described. Accordingly, departures may be made from such details without departing from the spirit or scope of the general inventive concept.

Having described the invention, what is claimed is:

1. An intubation guide comprising:
   an elongated aft member with a support member depending from a distal end of the aft member;
   a guide wall pivotally mounted to the aft member in spaced relationship to the support member; and
   a generally flexible spout extending from the aft member and toward the guide wall.

2. The intubation guide of claim 1 further comprising a side arm interconnecting the guide wall and aft member.

3. The intubation guide of claim 2, the side arm being rigidly connected to the guide wall and pivotally mounted to the aft member.

4. The intubation guide of claim 2, the side arm including a mounting post, the aft member including a post receiving channel, the mounting post being rotatably held in the post receiving channel whereby the guide wall pivots relative to the aft member by rotation of the mounting post in the post receiving channel.

5. The intubation guide of claim 2 further comprising cooperating stop structure associated with the aft member and the side arm, whereby to limit the extent of pivoting of the guide wall relative to the aft member.

6. The intubation guide of claim 5, the stop structure including a stop block socket formed on the aft member and a stop block formed on the arm.

7. The intubation guide of claim 5, the stop structure including a shoulder socket formed on the aft member and a shoulder formed on the arm.

8. The intubation guide of claim 1, the guide wall being pivotally mounted to the distal end of the aft member.

9. The intubation guide of claim 8, the guide wall being pivotally mounted to the support member.

10. The intubation guide of claim 1, the flexible spout being a separate piece mounted to the aft member.

11. The intubation guide of claim 1, the aft member being generally rigid, the flexible spout being formed integrally therewith.

12. The intubation guide of claim 1, the aft member including an extending handle portion.

13. An intubation guide comprising:
   an elongated aft member with a support member depending from a distal end of the aft member;
   a rigid guide wall; and
   a side arm connected to the guide wall, the guide wall being pivotally mounted to the aft member through the side arm and in spaced relationship to the support member so as to define an intubation tube passageway between the guide wall and the support member.

14. The intubation guide of claim 13, the side arm including a mounting post, the aft member including a post receiving channel, the mounting post being rotatably held in the post receiving channel whereby the guide wall pivots relative to the aft member by rotation of the mounting post in the post receiving channel.

15. The intubation guide of claim 13 further comprising cooperating stop structure on the aft member and the side arm, whereby to limit the extent of pivoting of the guide wall relative to the aft member.

16. The intubation guide of claim 15, the stop structure including a stop block socket formed on the aft member and a stop block formed on the arm.

17. The intubation guide of claim 15, the stop structure including a shoulder socket formed on the aft member and a shoulder formed on the arm.

18. The intubation guide of claim 13, the guide wall being pivotally mounted to the distal end of the aft member.

19. The intubation guide of claim 18, the guide wall being pivotally mounted to the support member.

20. The intubation guide of claim 13, the aft member including an extending handle portion.

21. The intubation guide of claim 13 further comprising a spout extending from the aft member and toward the guide wall.

22. An intubation guide comprising:
   an elongated aft member with a support member depending from a distal end of the aft member;
   a guide wall in spaced relationship to the support member; and
   a generally flexible spout extending from the aft member and toward the guide wall.

23. The intubation guide of claim 22, the flexible spout being a separate piece mounted to the aft member.

24. The intubation guide of claim 22, the aft member being generally rigid, the flexible spout being formed integrally therewith.

25. The intubation guide of claim 22, the aft member including an extending handle portion.

26. The intubation guide of claim 22 wherein the spout has a concave cross section.

27. A method of inserting an orotracheal tube into a laryngeal opening in a patient's throat comprising:
   mounting an orotracheal tube to an intubation guide having an aft member with a support member depending from the aft member and a guide wall spaced from the support member by a distance, the tube being mounted on the aft member so as to extend against the guide wall;
   inserting the guide wall into the patient's throat and against a back wall thereof with a portion of the aft member situated over the patient's tongue, and with the guide wall in a first position whereat the distance has a magnitude;
   pivoting the guide wall relative to the aft member from a first position toward a second position whereby to decrease the magnitude of the distance;
   continuing to insert the guide wall into the patient's throat until the support member is over the back of the tongue;
   applying traction on the support member to pull the back of the tongue away from the back of the throat to enlarge the area at the back of the throat and align the space between the guide wall and the support member over the larynx for insertion of the orotracheal tube into the laryngeal opening through the space.

28. The method of claim 27 further comprising applying traction on the support member in cooperation with pivoting the guide wall back toward the first position whereby to increase the magnitude of the distance.

29. The method of claim 27 wherein the intubation guide includes a spout normally extending from the aft member towards the guide wall, the method including mounting the orotracheal tube so as to extend over the spout.

30. The method of claim 29 further comprising deforming the spout from a first form to a second form in cooperation with pivoting of the guide wall.

31. The method of claim 30 further comprising allowing the spout to flex back from the second form toward the first form in cooperation with applying traction on the support member.

32. The method of claim 31 further comprising applying traction on the support member in cooperation with pivoting the guide wall back toward the first position whereby to increase the magnitude of the distance.

* * * * *

UNITED STATES PATENT AND TRADEMARK OFFICE
CERTIFICATE OF CORRECTION

PATENT NO.    : 6,672,305 B2  
DATED         : January 6, 2004  
INVENTOR(S)   : Jeffrey D. Parker It is certified that error appears in the above-identified patent and that said Letters Patent is hereby corrected as shown below:

<u>Title page,</u>  
Item [56], References Cited, FOREIGN PATENT DOCUMENTS, add -- AR 289094 --

<u>Column 8,</u>  
Lines 40-44, "a generally flexible spout extending from the aft member and toward the guide wall." should read --a spout extending from the aft member and toward the guide wall, wherein the spout is sufficiently flexible to cooperate with the guide wall to avoid unduly bending an orotracheal tube.--

<u>Column 9,</u>  
Lines 15-20, "the guide wall being privotally mounted to the aft member through the side arm and in spaced relationship to the support member so as to define an intubation tube passageway between the guide wall and the support member." should read --the side arm pivotally mounted to the aft member whereby to pivotally support the guide wall; the guide wall and the support member defining a tube receiving space adapted to receive an orotracheal tube.--

Lines 50-51, "a generally flexible spout extending from the aft member and toward the guide wall." should read --a spout extending from the aft member and toward the guide wall, wherein the spout is sufficiently flexible to cooperate with the guide wall to avoid unduly bending an orotracheal tube.--

<u>Column 10,</u>  
Line 13, "by a distance, the tube being" should read -- by a distance so as to define a tube receiving space to receive the orotracheal tube, the tube being --  
Lines 29 and 31, "space" should read -- tube receiving space -- (both occurrences)

Signed and Sealed this

Twenty-seventh Day of April, 2004

JON W. DUDAS  
*Acting Director of the United States Patent and Trademark Office*